(12) United States Patent
Dahms et al.

(10) Patent No.: US 8,623,809 B2
(45) Date of Patent: Jan. 7, 2014

(54) PEARLESCENT CONCENTRATE AND PROCESS FOR PRODUCTION

(75) Inventors: Gerd H. Dahms, Duisburg (DE); Andreas H. Jung, Duisburg (DE)

(73) Assignee: OTC GmbH, Oberhasuen (DE)

( * ) Notice: Subject to any disclaimer, the term of this patent is extended or adjusted under 35 U.S.C. 154(b) by 0 days.

(21) Appl. No.: 13/392,242

(22) PCT Filed: Aug. 27, 2010

(86) PCT No.: PCT/EP2010/062576
§ 371 (c)(1), (2), (4) Date: Feb. 24, 2012

(87) PCT Pub. No.: WO2011/023803
PCT Pub. Date: Mar. 3, 2011

(65) Prior Publication Data
US 2012/0149629 A1 Jun. 14, 2012

(30) Foreign Application Priority Data
Aug. 27, 2009 (DE) .................... 10 2009 040 455

(51) Int. Cl.
*C11D 17/00* (2006.01)
(52) U.S. Cl.
USPC ........... 510/424; 510/426; 510/428; 510/499; 510/506
(58) Field of Classification Search
None
See application file for complete search history.

(56) References Cited

U.S. PATENT DOCUMENTS

| | | | |
|---|---|---|---|
| 5,711,899 A | 1/1998 | Kawa et al. | |
| 6,147,124 A | 11/2000 | Ansmann et al. | |
| 6,165,955 A | 12/2000 | Chen et al. | |
| 6,228,831 B1 | 5/2001 | Ansmann et al. | |
| 6,235,702 B1 | 5/2001 | Ansmann et al. | |
| 6,727,217 B1 | 4/2004 | Nieendick et al. | |
| 6,835,700 B1 | 12/2004 | Nieendick et al. | |
| 7,268,107 B2 | 9/2007 | Nieendick et al. | |
| 2004/0086470 A1 | 5/2004 | Nieendick et al. | |
| 2005/0158270 A1* | 7/2005 | Frantz et al. | 424/70.24 |

FOREIGN PATENT DOCUMENTS

| | | |
|---|---|---|
| DE | 3617306 | 11/1986 |
| EP | 0568848 | 11/1993 |
| WO | 9836048 | 8/1998 |
| WO | 9909944 | 3/1999 |

OTHER PUBLICATIONS

International Search Report, PCT/EP2010/062576, dated Apr. 6, 2011, 9 pages.
International Preliminary Report on Patentability, PCT/EP2010/062576, dated Mar. 6, 2012, 11 pages.

* cited by examiner

*Primary Examiner* — Necholus Ogden, Jr.
(74) *Attorney, Agent, or Firm* — Senniger Powers LLP

(57) ABSTRACT

The invention relates to pumpable aqueous pearlescent concentrates having a high active content of alkyl sulfates, alkyl ether sulfates, alkyl sulfonates, mono and diesters of sulfosuccinic acid (sulfosuccinates), alkyl glycinates, alkyl sarcosinates, and/or alkyl taurates, and fatty acid glycol esters and/or carbolic acid amides as pearlescent agents, and to a method for the production thereof. The pearlescent concentrates according to the invention are suitable as additives for improving the optical appearance of tenside components, for example of liquid washing and cleaning agents or liquid body wash and body care agents and hair care agents. The pearlescent concentrates according to the invention comprise 35 to 85% by weight of a dispersant selected from alkyl ether sulfates, alkyl sulfates, alkyl sulfonates, mono and diesters of sulfosuccinic acid, alkyl glycinates, alkyl sarcosinates and/or alkyl taurates, and mixtures thereof, 15 to 40% by weight of a pearlescent agent component selected from fatty acid glycol esters, fatty acid alkanol amides and mixtures thereof, optionally advantageous additives and water in the quantity short of 100% by weight, but not in a concentration greater than 30% by weight.

17 Claims, 2 Drawing Sheets

PEARLESCENT CONCENTRATE AND PROCESS FOR PRODUCTION

REFERENCE TO RELATED APPLICATIONS

This application is the U.S. national stage application of International Patent Application No. PCT/EP2010/062576, filed Aug. 27, 2010, and claims the benefit of German Application No. 102009040455.4, filed Aug. 27, 2009, the entire disclosures of which are incorporated herein by reference.

FIELD OF THE INVENTION

The invention relates to pumpable aqueous pearlescent concentrates having a high active content of alkyl sulfates, alkyl ether sulfates, alkyl sulfonates, mono- and diesters of sulfosuccinic acid (sulfosuccinates), alkyl glycinates, alkyl sarcosinates and/or alkyl taurates and also fatty acid glycol esters and/or carboxamides as pearlescers, and to processes for their production.

BACKGROUND OF THE INVENTION

For improving the optical appearance of surfactant compositions, for example liquid detergents and cleansing agents (i.e. floor cleansing agents, washing-up liquids or similar products) or liquid body cleansing and body care compositions as well as hair treatment compositions (i.e. shampoos, bath additives, liquid soaps, shower gels or similar products), aqueous pearlescent dispersions (pearlescent concentrates) are frequently added to these, whereby a pearlescence and thus an esthetically pleasing external appearance is imparted to the surfactant compositions.

The known aqueous pearlescent dispersions consist essentially of at least one pearlescent compound (also called a pearlescent component or pearlescer), at least one dispersant (also called a solvent, wetting agent or emulsifier) and water. Numerous pearlescent compounds and compound mixtures are recommended in the prior art, for example fatty acids, fatty acid mono- or fatty acid dialkanolamides, monoesters or diesters of alkylene glycols such as ethylene glycol, propylene glycol or oligomers thereof with fatty acids (fatty acid glycol esters) and also monoesters or polyesters of glycerol with higher fatty acids. Even more numerous are the compounds that are described as dispersants, for example alkyl sulfates, alkyl ether sulfates, alkyl sulfonates, amine oxides, betaines, addition products of ethylene oxide and/or propylene oxide to fatty alcohols, fatty acids or alkylphenols and also glycerol mono- or glycerol diesters or sorbitan mono- or sorbitan diesters of fatty acids, in which the glycerol esters and sorbitan esters are optionally ethoxylated and/or propoxylated, alkyl mono- or alkyl oligo-glycosides and the like.

The immediate prior art is very well represented in the following patents and patent applications.

U.S. Pat. No. 7,268,107 discloses a pearlescent composition that contains from about 30 to 55% by weight of a pearlescent wax, a nonionic dispersant, optionally a zwitterionic dispersant, about 0.1% by weight to 5% by weight of a polyol ester and water, in which the active content (sum of the content of pearlescent component and dispersant) is at least about 55% by weight based on the weight of the composition and the sum of the content of dispersants is less than 25% by weight based on the weight of the composition and in which the nonionic dispersant and the polyester are present in a weight ratio of about 5:1 to 10:1.

US patent application US 2004/0086470 A1 relates to an aqueous pearlescent composition that contains approximately 30 to 60% by weight of a wax component, which consists to at least 15% by weight, based on the weight of the wax component, of amorphous particles and to at most 85% by weight, based on the weight of the wax component, of crystalline particles, and approximately 5 to 25% by weight of a surfactant, selected from a nonionic surfactant, an amphoteric surfactant and mixtures thereof.

U.S. Pat. No. 6,727,217 B1 relates to a process for the production of pearlescent surfactant compositions at a temperature of approximately 10° C. to 45° C., in which an aqueous surfactant solution is contacted with a composition of a pearlescent wax and a polyol ester.

U.S. Pat. No. 6,835,700 B1 discloses a fluid pearlescent concentrate that comprises approximately 25 to 45% by weight of a pearlescent wax, approximately 35 to 40% by weight of a nonionic, amphoteric, zwitterionic and/or cationic dispersant, approximately 0.5 to 15% by weight of a polyol ester and water, in which the sum of the content of wax, dispersant and polyol ester is at least 55% by weight.

U.S. Pat. No. 6,147,124 A relates to fluid, bio-degradable pearlescent concentrates that contain 5 to 50% by weight of an alkanol ether or of an alkanolamide as the pearlescent component, 5 to 55% by weight of a fatty acid M-alkyl polyhydroxyalkylamide as the sole nonionic dispersant and 0.1 to 40% by weight of a low molecular weight polyol.

U.S. Pat. No. 6,235,702 B1 relates to an aqueous pearlescent concentrate that contains 1 to 99% by weight (based on the total weight) of an ester of a hydroxyl group-bearing carboxylic acid with a fatty alcohol, 0.1 to 90% by weight (based on the total weight) of a dispersant, selected from an anionic surfactant, a nonionic surfactant, a cationic surfactant, a zwitterionic surfactant, an ester quat and mixtures of these, and up to 40% by weight (based on the total weight) of a polyol.

U.S. Pat. No. 6,228,831 B1 discloses a pearlescent concentrate that contains 1 to 99.9% by weight of a fatty component, selected from the group consisting of fatty alcohols, fatty ketones, fatty ethers, fatty carbonates and mixtures of these, 1 to 99.9% by weight of a dispersant selected from the group consisting of anionic, nonionic, cationic, ampholytic and zwitter-ionic surfactants and mixtures of these, and up to 40% by weight of a polyol.

U.S. Pat. No. 5,711,899 relates to fluid pearlescent concentrates that contain 15 to 40% by weight of a pearlescent component, 5 to 55% by weight of a nonionic, ampholytic and/or zwitterionic surfactant and 0.1 to 5% by weight of a low molecular weight polyol.

U.S. Pat. No. 6,165,955 relates to a pearlescent concentrate with high temperature stability, that consists of a pearlescer based on a fatty acid selected from the group consisting of hydroxylstearates, polyethylene glycol mono- and distearates, ethylene glycol mono- and distearates, stearic acid monoethanolamide and mixtures of these, in which at least 90% by weight of the fatty acids of said fatty acid constituent consist of octadecanoic acid.

European patent application EP 0 568 848 A1 relates to fluid aqueous pearlescent dispersions that essentially consist of a fatty acid glycol ester as the pearlescence-imparting component, of two specific surfactant compounds, namely a betaine and a fatty alcohol alkoxylate, and water in a specific amount in each case.

Such pearlescent formulations additionally contain, besides the alkyl ether sulfates and/or alkyl sulfates and/or alkyl sulfonates employed in surfactant compositions as key substances, a series of auxiliaries such as, for example, amine oxides, betaines, addition products of ethylene oxide and/or propylene oxide to fatty alcohols, fatty acids or alkylphenols, glycerol mono- or glycerol diesters or sorbitan mono- or sorbitan diesters of fatty acids; in which the glycerol esters and sorbitan esters are optionally ethoxylated and/or propoxylated, alkyl mono- or alkyl oligo-glycosides, alcohols, polyols and the like.

The concentration of the key substances employed here is in general less than 35% by weight. Such lowly concentrated pearlescent formulations mainly have economic disadvantages. In direct comparison to the highly concentrated pearlescent formulations, transport, packaging and storage costs in particular matter here.

The production of pearlescent dispersions in the prior art generally takes place batchwise in stirred reactors. In this process, the necessary amounts of the substances employed are metered into a mixing vessel, heated to 5-20° C. above the melting temperature of the highest-melting component and mixed. After mixing, the mixture is first cooled to 30-40° C. with stirring without cooling. Only after reaching this temperature is it cooled to room temperature using cooling.

A check generally takes place only on the finished product of the corresponding mixing batch. Continuous checking of the production process is generally not possible.

In addition, highly concentrated pearlescent dispersions can generally not be produced by the conventional processes, as due to the high viscosity of such compositions problems in the thorough mixing of the components occur. On account of the high energy input by the stirrer necessary for thorough mixing, such processes are on the one hand very energy- and cost-intensive and on the other hand the stirred material is very strongly heated, which in turn adversely affects the quality of the product.

Moreover, a variation of the amounts of product in the prior art is only possible to a very restricted extent, since the possible batch size with a batch mixer lies in a narrowly restricted range. The minimal batch size must generally not fall below half of the maximum batch size.

The patent application WO 2004/082817 A1 discloses an apparatus and a process for the continuous production of emulsions or dispersions. The apparatus described comprises a mixing vessel closed on all sides, that has supply and outlet pipes for the entry and discharge of fluid substances or substance mixtures as well as a stirrer and that allows a stirred entry into the emulsion or dispersion without production of cavitation forces and without high-pressure homogenization.

SUMMARY OF THE INVENTION

The object of the invention consists in making available a readily pumpable, aqueous pearlescent concentrate with a high proportion of active substances and excellent pearlescent character, that can be cold-processed and thus easily handled using conventional mixing technology, which is also suitable for the processing of highly concentrated conventionally employed alkyl ether sulfates to detergents and cleansing agents, as well as novel processes for the production of these highly concentrated pearlescent concentrates.

DETAILED DESCRIPTION OF PREFERRED EMBODIMENTS

Figure 1:
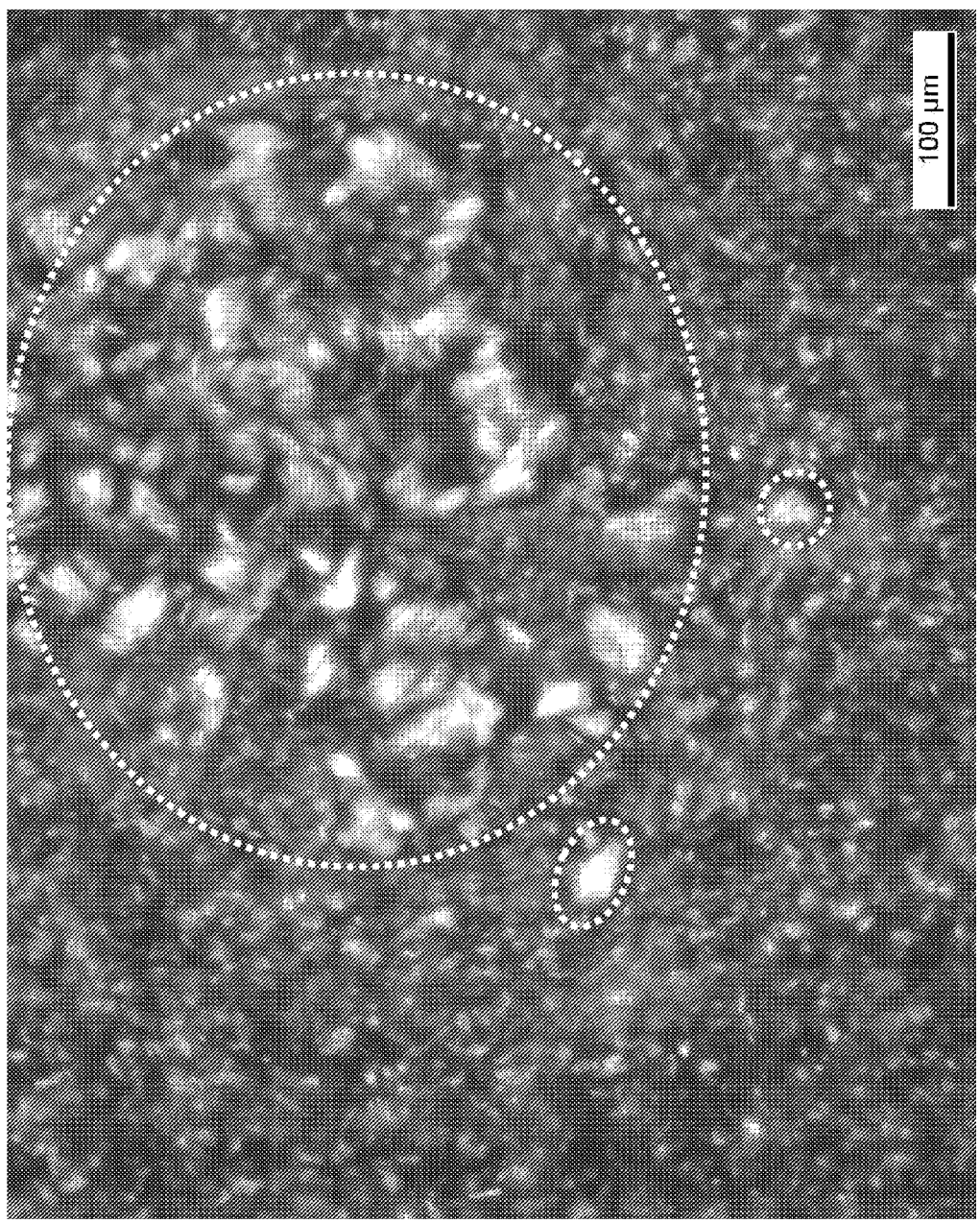
FIG. 1 is a photograph of a prior art pearlescent dispersion.

The object is achieved by a pumpable aqueous pearlescent concentrate, which comprises the following constituents:

a) One or more alkyl ether sulfates, alkyl sulfates, alkyl sulfonates, mono- and diesters of sulfosuccinic acid (sulfosuccinates), alkyl glycinates, alkyl sarcosinates and/or alkyl taurates or a combination of these as dispersants with a proportion of 35 to 85% by weight, based on the total weight of the concentrate.

b) 15 to 40% by weight, based on the total weight of the concentrate, of a pearlescent component, selected from the group consisting of
fatty acid glycol esters according to the general formula (I)

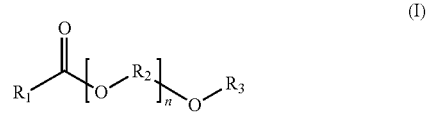

in which $R_1$ is an alkyl radical with 12 to 22 C atoms
$R_2$ is a divalent radical of the formula —$C_2H_4$— or —$C_3H_5$—,
$R_3$=H or a radical of the formula

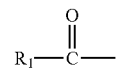

and n is a number from 1 to 10,
fatty acid alkanolamides according to the general formula (II)

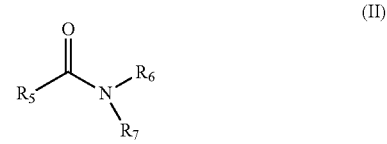

in which $R_5$ is an alkyl radical with 8 to 22 C atoms,
$R_6$=H, an alkyl radical with 1 to 4 C atoms, —($CH_2$—$CH_2$—O)$_n$—$R_8$,
—($CH_2$—CH($CH_3$)—$CH_2$—O)$_n$—$R_8$ with n=1 to 10,
$R_7$=H, an alkyl radical with 1 to 4 C atoms, —($CH_2$—$CH_2$—O)$_n$—$R_8$,
—($CH_2$—CH($CH_3$)—$CH_2$—O)$_n$—$R_8$ with n=1 to 10 and
$R_8$=H, methyl, ethyl, n-propyl, propyl, n-butyl, i-butyl or t-butyl,
and mixtures thereof, c) If appropriate, expedient additives such as preservatives, buffer substances, inorganic or organic electrolytes, alcohols, fatty alcohols, fatty acids and/or their ethoxylates, in particular PEG-x-glyceryl laurates and/or PEG-x-glyceryl cocoates in which x=1 to 10.

d) water in the amount missing to 100% by weight, but not with a concentration higher than 30% by weight, preferably 25% by weight, based on the total weight of the concentrate.

The dispersants or pearlescers employed according to the invention can contain one or more different compounds from the respective groups.

The sum of the content of the pearlescence-imparting compound and the content of dispersant is defined as the active content of the pearlescent concentrate and is preferably >60% by weight, preferably 65 to 85% by weight, particularly preferably 70 to 80% by weight.

The sum of the water and additives content of the pearlescent concentrate is preferentially less than 30% by weight, preferably 25% by weight, based on the total amount of the pearlescent concentrate.

The aqueous pearlescent concentrate according to the invention preferentially has a content of 35 to 85% by weight, preferably 40 to 70% by weight, particularly preferably 50 to 60% by weight, of one or more alkyl ether sulfates, alkyl sulfates, alkyl sulfonates, mono- and diesters of sulfosuccinic acid (sulfosuccinates), alkyl glycinates, alkyl sarcosinates and/or alkyl taurates. The alkyl ether sulfate, alkyl sulfate, alkyl sulfonate, sulfosuccinate, alkyl glycinate, alkyl sarcosinate and/or alkyl taurate acts here as a dispersant, which stabilizes the pearlescent dispersion according to the invention. Commercially obtainable alkyl ether sulfates, alkyl sulfates, alkyl sulfonates, sulfosuccinates, alkyl glycinates, alkyl sarcosinates and/or alkyl taurates are customarily marketed and processed as aqueous solutions, in which the concentrations are customarily 70% aqueous solutions or thereunder.

The total concentration of pearlescent component is 15 to 40% by weight based on the total weight of the concentrate. The fatty acid glycol esters and the fatty acid alkanolamides can here be present in the pearlescent concentrate according to the invention either individually or as a mixture. Preferably, the total concentration of pearlescent component in the pearlescent concentrate according to the invention is 15 to 30% by weight, particularly preferably 20 to 25% by weight, based on the total weight of the concentrate.

The aqueous pearlescent concentrate according to the invention can advantageously be incorporated into the customary surfactant compositions without difficulties. Particularly preferably, the incorporation into the surfactant composition takes place in cold form, i.e. preferably at a temperature below 25° C., particularly preferably at room temperature. Part of the invention is therefore also a surfactant composition containing a pearlescent concentrate according to the invention. Advantageously, the use of a relatively small amount of pearlescent concentrate also already imparts a pearlescent appearance to the surfactant composition. Suitable proportions of pearlescent concentrate in a surfactant composition, depending on the pearlescent effect desired, are between 0.5 and 10% by weight, preferably between 0.5 and 5% by weight, particularly preferably between 0.5 and 2% by weight.

Pearlescent dispersions having the high concentration of active content according to the invention offer both ecological and economical advantages compared to conventionally available dispersions. The small water content lowers both the transport and the storage costs considerably. It is particularly advantageous that the pearlescent concentrates according to the invention can be prepared for further processing in preservative-free form. The restriction of the dispersant to the alkyl sulfates, alkyl ether sulfates, alkyl sulfonates, mono- and diesters of sulfosuccinic acid (sulfosuccinates), alkyl glycinates, alkyl sarcosinates and/or alkyl taurates anyway employed in detergents and cleansing agents moreover advantageously allows the formulator of detergents and cleansing agents much more freedom in the final composition of his product.

The invention is based on the surprising finding that aqueous alkyl ether sulfates, alkyl sulfates, alkyl sulfonates, mono- and diesters of sulfosuccinic acid (sulfosuccinates), alkyl glycinates, alkyl sarcosinates and/or alkyl taurates having a content of 40 to 90% by weight based on the total weight of the concentrate can be processed with pearlescence-imparting compounds such as fatty acid glycol esters and/or carboxamides to give pumpable pearlescent concentrates, whose active content is above 60% by weight, preferably 65 to 85% by weight, particularly preferably 70 to 80% by weight.

Counterions that can be employed for the aqueous alkyl ether sulfates, alkyl sulfates, alkyl sulfonates, mono- and diesters of sulfosuccinic acid (sulfosuccinates), alkyl glycinates, alkyl sarcosinates and/or alkyl taurates used as dispersants are any organic and inorganic countercations, as long as the alkyl ether sulfates, alkyl sulfates, alkyl sulfonates, mono- and diesters of the sulfosuccinic acid (sulfosuccinates), alkyl glycinates, alkyl sarcosinates and/or alkyl taurates remain readily soluble or dispersible in water and as long as the counterions are physically and chemically compatible with the basic constituents of the pearlescent concentrate and do not disadvantageously influence the product characteristics such as pearlescence, stability or processability. Preferred counterions are alkali metal ions such as sodium and/or potassium, alkaline earth metal ions such as calcium and/or magnesium as well as substituted and unsubstituted ammonium ions such as monoethanolamine, diethanolamine, triethanolamine and triisopropanolamine.

The alkyl ether sulfates employed are preferably the sulfates of fatty alcohols having a chain length of 8 to 16 C atoms, e.g. sodium lauryl ether sulfate, ammonium lauryl ether sulfate, triethylamine lauryl ether sulfate, triethanolamine lauryl ether sulfate, magnesium lauryl ether sulfate, sodium C12-13 pareth sulfate, and the Na salt of lauryl myristyl ether sulfate.

Preferred alkyl sulfates are sodium lauryl sulfate, ammonium lauryl sulfate, triethylamine lauryl sulfate, triethanolamine lauryl sulfate, magnesium lauryl sulfate, ammonium cocoyl sulfates, sodium cocoyl sulfates and the Na and/or Mg salts of lauryl myristyl sulfate.

The alkylsulfonates preferentially employed are sodium tridecylbenzenesulfonate, sodium dodecylbenzene-sulfonate, olefin sulfonate, dodecylbenzene sulfonate and $C_{14}$-$C_{16}$-paraffin sulfonate.

Preferably, the mono- and diesters of sulfosuccinic acid (sulfosuccinates) are esters of sulfosuccinic acid with C8-C16-fatty alcohols, fatty alcohol polyglycol ethers or alkylphenol polyglycol ethers. Preferentially, these are selected from sodium dioctylsulfosuccinate, sodium diisooctylsulfosuccinate and polyglycol ether sulfosuccinyl acid esters of C8-C16-fatty alcohols.

The alkyl glycinates preferably employed are sodium lauryl glycinate, sodium lauroyl glycinate, sodium myristyl glycinate and/or sodium cocoyl glycinate.

The alkyl sarcosinates preferably employed are sodium lauryl sarcosinate, sodium lauroyl sarcosinate, sodium myristyl sarcosinate and/or sodium cocoyl sarcosinate.

Preferred alkyl taurates, that is salts of taurine (2-aminoethanesulfonic acid), which are occasionally also described as alkyl taurinates, are sodium methylcocoyltaurate and/or sodium methylmyristyltaurate.

Preferentially, alkyl ether sulfates, alkyl sulfates and/or alkyl sulfonates are employed from the aforementioned compounds as dispersants. Alkyl ether sulfates are particularly preferred.

The fatty acid glycol esters contained in the pearlescent concentrate according to the invention as a pearlescent component correspond to the general formula (I), in which $R_1$ is an alkyl radical with 12 to 22 C atoms, $R_2$ is a divalent radical of the formula —$C_2H_4$— or —$C_3H_5$—, $R_3$=H or a radical of the formula

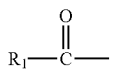

and n is a number from 1 to 10.

$R_1$ is preferably a saturated or unsaturated alkyl radical with 12 to 18 C atoms, $R_2$ is preferably —$C_2H_4$—, $R_3$ is preferably $R_1$—CO— and n is preferably a number from 1 to 3. If the alkyl radical $R_1$ is unsaturated, it preferentially contains 1 to 3 double bonds.

Particularly preferred pearlescent components are mono- and diesters of ethylene glycol, diethylene glycol or triethylene glycol with palmitic acid, stearic acid, oleic acid, tallow fatty acid, coconut fatty acid and/or other fatty acids, e.g. ethylene glycol monostearate, ethylene glycol distearate and diethylene glycol distearate.

The fatty acid alkanolamides contained in the pearlescent concentrate according to the invention as a pearlescent component correspond to the general formula (II) in which $R_5$ is an alkyl radical with 8 to 22 C atoms, $R_6$=H, an alkyl radical with 1 to 4 C atoms, —$(CH_2$—$CH_2$—$O)_n$—$R_8$, —$(CH_2$—$CH(CH_3)$—$CH_2$—$O)_n$—$R_8$ with n=1 to 10, $R_7$=H, an alkyl radical with 1 to 4 C atoms, —$(CH_2$—$CH_2$—$O)_n$—$R_8$, —$(CH_2$—$CH(CH_3)$—$CH_2$—$O)_n$—$R_8$ with n=1 to 10 and $R_8$=H, methyl, ethyl, n-propyl, i-propyl, n-butyl, i-butyl or t-butyl.

Preferred fatty acid alkanolamides are ethanolamide derivatives of alkanoic acids with 8 to 22 C atoms, preferably 12 to 18 C atoms. The particularly suitable compounds include lauric acid, myristic acid, palmitic acid and stearic acid monoethanolamides, e.g. coconut fatty acid monoethanolamide, lauroyl monoethanolamide, myristoyl monoethanolamide, palmitoyl monoethanolamide and stearoyl monoethanolamide.

In a preferred embodiment of the pearlescent concentrate according to the invention, the fatty acid alkanolamides comprise at least 60%, preferably at least 70%, particularly preferably at least 75%, of alkanoic acid derivatives with 12.C atoms.

The mother of pearl-like luster of pearlescent dispersions is based on the presence of lamellar lyotropic liquid crystalline structures. In order that such lamellar structures can form, an optimal ratio between emulsifier and pearlescer must exist, which depends on the geometry of the participating pearlescers and dispersants. The parameter for this is the "critical packing parameter". If the critical packing parameter adopts values of ~1, an optimal composition has been found and optimal conditions for the formation of a lamellar phase prevail. Ways are known to the person skilled in the art to adjust the critical packing parameter for a specific combination of pearlescer and dispersant by the variation of the amounts employed. In addition, means are known to the person skilled in the art by which the critical packing parameter can be selectively changed, such as, for example, the addition of a long-chain alcohol, amine or of another amphiphilic molecule or the addition of a salt. Preferably, the pearlescent concentrates contain no other surfactants than the abovementioned dispersants and pearlescers.

For the formation of the lamellar lyotropic liquid crystalline structures, the pearlescent concentrates according to the invention need a certain amount of water, which is intercalated between the lamellar bilayers of the amphiphilic molecules contained (dispersants and pearlescers). Preferably, the minimum content of water is 5% by weight, particularly preferably 10% by weight, very particularly preferably 15% by weight, based on the total weight of the concentrate. Depending on the amphiphilic substances used, the lamellar system can absorb a certain amount of water here, a process that is described as swelling. If the point is reached at which the concentrate is completely swollen and the swellability of the surface-active substances contained in the concentrate is exceeded, the free water that can no longer be bound collects as "bulk water".

The pearlescent concentrate according to the invention preferentially has a high phase volume ratio, i.e. the amount of water in relationship to the amphiphilic molecules contained is low. On the one hand, this guarantees the advantages that are associated with a high active content (see above), on the other hand, the formation of lyotropic liquid crystalline lamellar structures is favored.

The pearlescent concentrates according to the invention are preferentially completely swollen here. To ensure this, the proportion of water is preferably chosen such that it is slightly above the maximum which can be bound in the lamellar structures. Preferentially, the pearlescent concentrates according to the invention contain a proportion of bulk water of 0.5 to 15% by weight, preferably 1 to 10% by weight, based on the total amount of the pearlescent concentrate.

The phase volume ratio can be, determined by means of rheological test methods. It is widely known that the viscosity increases exponentially with increasing internal phase. The viscosity maximum is reached at the point when a bulk water phase no longer exists and all water is bound interlamellarly. Another test method for the determination of the phase volume ratio is measurement of the conductivity. This decreases exponentially with increasing internal phase and reaches the zero value when all water is bound interlamellarly.

The pearlescent dispersions known from the prior art do not consist completely of swollen lamellar liquid crystalline structures, but contain large portions of unswollen structures consisting of pearlescer and/or dispersant, in which an inadequate amount of water is bound. Such a commercially obtainable pearlescent dispersion is depicted in FIG. 1. As can easily be discerned, in addition to completely swollen areas, which have a uniform granular structure, the concentrate also contains large inhomogeneous areas, which stand out clearly visually and which are not completely swollen. This is caused by the batch processes customarily employed in the prior art, during which the presence of dead spaces and the formation of temperature gradients during cooling can scarcely be avoided.

This results in pearlescent dispersions that are prepared according to the processes known in the prior art having a poor storage stability, in particular at elevated temperatures from about 35° C. If the pearlescent dispersions known from the prior art are heated to temperatures above this point, the bulk water present begins to intercalate into the unswollen areas of the pearlescent dispersion, new lamellar structures are formed and the viscosity of the composition increases up to more than 10-fold. The compositions can then no longer be readily processed.

Figure 2:
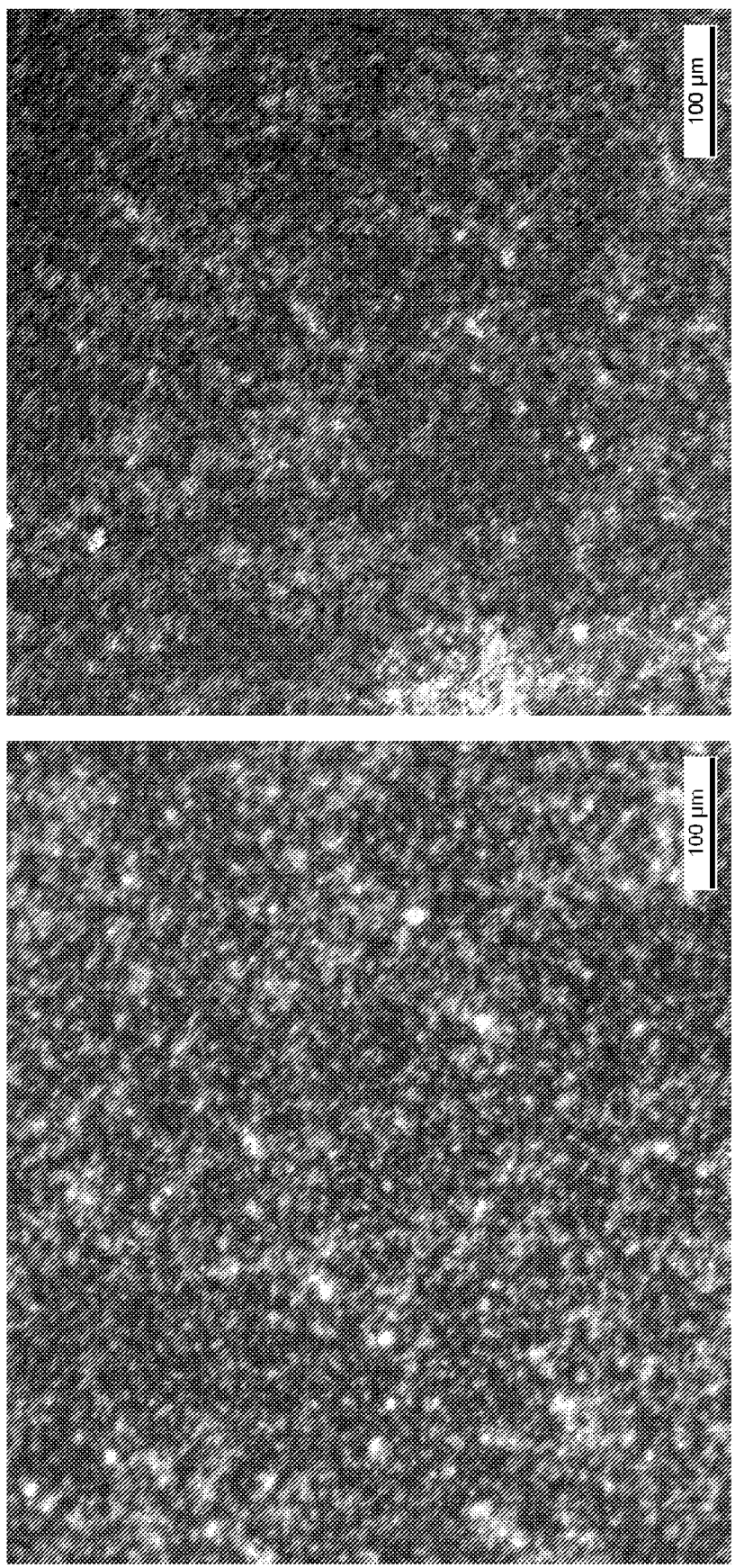
FIG. 2 is a photograph of the pearlescent dispersion of the invention.

The pearlescent compositions according to the invention, on the other hand, are completely swollen. A pearlescent concentrate according to the invention, which is distinguished by a high homogeneity and the absence of unswollen areas, is shown in FIG. 2. A further intercalation of bulk water and a viscosity increase accompanying it is thus not possible. As a result of a temperature increase to 35° C., preferably over 45° C., the viscosity of the pearlescent concentrates according to the invention also increases by not more than 20%, preferably not more than 10%, particularly preferably not more than 5%. The pearlescent concentrates according to the invention are thus advantageously stable on storage and readily processable.

For controlling the viscosity of a pearlescent dispersion, polyols are often added in the prior art. The pearlescent concentrates according to the invention, on the other hand, can advantageously do without the use of polyols. In one embodiment, the pearlescent concentrates according to the invention are therefore free of polyols. In terms of the invention, a polyol content of less than 0.5%, preferentially less than 0.1%, preferably less than 0.05% of polyols, based on the total volume of the pearlescent concentrate, is meant by "free of polyols". Very preferably, no free polyols are detectable in the compositions according to the invention.

Polyols in terms of the present invention preferably have two to twelve carbon atoms and two or more hydroxyl groups. In addition, the polyols can also comprise further functional groups. Examples of polyols are glycerol, ethylene, glycol, diethylene glycol, propylene glycol, butylene glycol, pentylene glycol, hexylene glycol, polyethylene glycol and sugar alcohols such as, for example, sorbitol or mannitol.

Using the conventional batchwise processes, the pearlescent concentrates according to the invention can only be obtained with great effort. Part of the invention is therefore also a process for the production of the pearlescent concentrates according to the invention, which comprises the following steps:

a) introduction of a dispersant selected from alkyl ether sulfates, alkyl sulfates, alkyl sulfonates, mono- and diesters of sulfosuccinic acid (sulfosuccinates), alkyl glycinates, alkyl sarcosinates and/or alkyl taurates or a combination thereof and a pearlescent component selected from one or more fatty acid glycol esters according to the general formula (I),

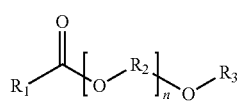

(I)

in which $R_1$ is an alkyl radical with 12 to 22 C atoms $R_2$ is a divalent radical of the formula $-C_2H_4-$ or $-C_3H_5-$, $R_3$=H or a radical of the formula

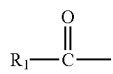

and n is a number from 1 to 10, and/or of one or more fatty acid alkanolamides according to the general formula (II)

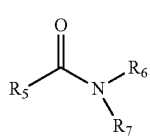

(II)

in which $R_5$ is an alkyl radical with 8 to 22 C atoms,
$R_6$=H, an alkyl radical with 1 to 4 C atoms, $-(CH_2-CH_2-O)_n-R_8$, $-(CH_2-CH(CH_3)-CH_2-O)_n-R_8$ with n=1 to 10, $R_7$=H, an alkyl radical with 1 to 4 C atoms, $-(CH_2-CH_2-O)_n-R_8$, $-(CH_2-CH(CH_3)-CH_2-O)_n-R_8$ with n=1 to 10 and $R_8$=H, methyl, ethyl, n-propyl, i-propyl, n-butyl, i-butyl or t-butyl, and optionally water in a first stirring step and thoroughly mixing at 55° C. to 90° C. in a lamellar fluid flow, in which the amount of water employed does not exceed 35% by weight, preferably 30% by weight, based on the concentration of the dispersants and pearlescers employed, such that a lamellar lyotropic liquid crystalline phase forms, b) cooling the resulting mixture by means of a cooling step to a temperature at which the pearlescent component crystallizes in the form of a liquid crystalline lamellar structure, c) Intensive mixing of the cooled mixture in a second stirring step and optionally dilution with the remaining amount of water, in which the temperature is kept below 45° C. by reduction of the stirring power and/or cooling of the stirring step, in which additives can be introduced either in the first or the second stirring step.

The dispersants or pearlescers introduced according to the invention can contain one or more different compounds from the respective groups.

The production of pearlescent systems demands a precise control of the process parameters (temperature, mixing time, duration and energy, flow course), as otherwise the pearlescent systems obtained vary greatly in their rheological, but also in their pearlescent, properties. The continuous production of the pearlescent systems is carried out, for example, with the aid of the apparatus for the continuous production of emulsions and dispersions described in the patent WO 2004/082817 by a selective combination of stirring and cooling steps.

In step a), the pearlescent components and the dispersant are introduced in the first stirring step by means of suitable pumps and mixed there at 55° C. to 90° C., preferably 70° C. to 80° C. If the components are fluid, prior heating is not necessary.

If one or more components are not fluid, for achieving a homogeneous melt the component(s) is/are heated to a temperature of 5-20° C. above its/their melting point(s). The mixing of the components in the first stirring step takes place in a lamellar fluid flow at 55° C. to 90° C., preferably 70° C. to 80° C. Optionally, the addition of a part or of the total amount of the water planned for in the formulation already takes place in the first stirring step. If one or more of the components employed in step a) is present as an aqueous solution or suspension, the addition of water, however, can also be completely dropped.

In the first process step a), the pearlescent components and the dispersant are converted into a coherent lamellar liquid crystalline phase. This lamellar phase consists of bilayers of the surface-active substances (pearlescers and dispersants), wherein the molecules are arranged tightly packed and in parallel, in which the hydrophobic and hydrophilic portions of the amphiphilic compounds are in each case aligned identically. Between the hydrophilic portions, water molecules can be inserted, a process which is described as swelling. The amount of water that can be absorbed by swelling varies depending on the dispersants and pearlescent agents used.

After mixing, the premixed mass is cooled in step b) by means of a cooling step such that the pearlescence-imparting component crystallizes out in the form of a liquid crystalline lamellar structure and the pearlescent effect appears. The temperature to which the mixture is cooled here is preferentially below 45° C., preferably 20° C. to 42° C., particularly preferably 30° C. to 40° C.

Finally, in step c) the cooled mass is mixed intensively with moderate stirring in a further stirring step and optionally diluted with the remaining amount of water. By this means, the viscosity of the concentrate is advantageously lowered to the extent that the concentrate can be readily processed further. Here, the temperature increase during mixing is preferably controlled such that the temperature of the product remains <45° C. This is preferably achieved either by lowering the stirring power and/or by intensive cooling of the stirring step.

As a result of the continuous processing of the components of the pearlescent concentrate, the use of mixing chambers of small dimensions is made possible. Advantageously, the energy input by the stirrer is minimized thereby and the rate of mixing and emulsion formation is maximized.

Likewise, the cooling step is also advantageously low-sized, whereby the formation of temperature gradients is minimized without the mixture to be cooled having to be stirred. By this means a rapid and satisfactory formation of a lamellar liquid crystalline phase occurs in the pearlescent concentrate to be produced. Preferably, the mixture is therefore not stirred in the cooling step of the process according to the invention.

As a result of the subsequent stirring in the second stirring step and/or the addition of water, in step c) the up to here coherent lamellar liquid crystalline phase is "torn" into small platelet-like particles, which are dispersed in the portion of water which is not interlamellarly bound. Here, the particles of the pearlescent concentrates according to the invention advantageously have a very homogeneous particle size distribution in the form of a Gaussian distribution. The particle size resulting from this can be selectively adjusted between 0.2 and 20 μm by choice of the stirring speed and residence period.

The process according to the invention is preferentially carried out at normal pressure or at pressures up to 10 bar, preferably up to 5 bar.

If appropriate additives are to be added to the pearlescent concentrate, these can be introduced in the first or in the second stirring step. Such appropriate additives can be, for example, electrolytes, e.g. sodium chloride, potassium chloride and/or magnesium chloride, preservatives, e.g. formic acid, or alternatively buffer substances and the like.

The invention is illustrated in more detail by the following figures and working examples, without being restricted to these. Here, FIG. 1 shows a light micrograph of a conventional pearlescent dispersions with unswollen areas (marked by dashed line) (measurement condition: linearly polarized light, 100 times magnification, polarizing filter) and FIG. 2 shows light micrographs of pearlescent concentrates according to the invention, which are completely swollen and have no unswollen areas (measurement conditions: linearly polarized light, 100 times magnification, polarizing filter).

WORKING EXAMPLE 1

Exemplary Formulations for the Pearlescent Concentrates According to the Invention

| Component | Trade description | % by weight | | | | | |
|---|---|---|---|---|---|---|---|
| | | 1 | 2 | 3 | 4 | 5 | 6 |
| Sodium lauryl ether sulfate* | Galaxy LES 70 | 70 | 80 | 80 | 80 | 85 | 80 |
| Ethylene glycol distearate | Galaxy 610 | 30 | 15 | 10 | 2.5 | | |
| Coconut fatty acid mono-ethanolamide | Galaxy 100 | | 5 | 10 | 17.5 | 15 | 20 |

*= 70% strength aqueous solution

WORKING EXAMPLE 2

Production of a Pearlescent Concentrate

The process is carried out in a two-stage apparatus, in which phase A and phase B are introduced separately in the first stirring step, and the output is cooled by means of a cooling step and led into the second stirring step. The percentage data are percentages by weight.

The amount produced per unit time can be specifically controlled by the variation of the residence times in the individual steps. For residence times in step 1-cooling step-step 2 of 20 s-53 s-20 s, approximately 60 kg of pearlescent concentrate can be produced per hour, for 16 s-41 s-16 s, approximately 80 kg of pearlescent concentrate per hour and for 10 s-26 s-10 s, approximately 120 kg of pearlescent concentrate per hour.

| Component | Tradename | |
|---|---|---|
| Phase A: | | |
| Sodium lauryl ether sulfate* | Galaxy LES 70 | 80% |
| Phase B: | | |
| Ethylene glycol distearate | Galaxy 610 | 10% |
| Coconut fatty acid monoethanolamide | Galaxy 100 | 10% |
| Peripheral velocity step 1 [m/s] | | 0.1-15 |
| Peripheral velocity step 2 [m/s] | | 0.1-15 |
| Residence time step 1 [s] | | 10-20 |
| Residence time cooling step [s] | | 30-60 |
| Residence time step 2 [s] | | 10-20 |

WORKING EXAMPLE 3

Experiments on Storage Stability

The viscosity behavior of pearlescent dispersions was investigated under shaking conditions on an orbital shaker (45° C. at 150 rpm). The results for two compositions according to the invention (1, 2; correspond to the compositions 1 and 2 from working example 1) and five commercially obtainable comparison compositions (3 to 7) are shown in the following table. The viscosity increase is shown in percentage of the starting viscosity of the respective composition. The viscosity axis is graduated logarithmically for presentation reasons.

| Composition | 6 h | 24 h |
|---|---|---|
| 1 | 0 | 0 |
| 2 | 0 | 0 |
| 3 | 50 | 135 |
| 4 | 1300 | 1330 |
| 5 | 129 | 344 |
| 6 | 88 | 182 |
| 7 | 0 | 33 |

It can be clearly discerned that under experimental conditions the conventional compositions exhibit a strong viscosity increase, however the compositions 1 and 2 do not. The viscosity of the compositions was determined by means of a cone-plate rheometer.

The invention claimed is:

1. A pumpable aqueous pearlescent concentrate, comprising
   a) 35 to 85% by weight of a dispersant of the group consisting of alkyl ether sulfates, alkyl sulfates, alkyl sulfonates, mono- and diesters of sulfosuccinic acid, alkyl glycinates, alkyl sarcosinates and/or alkyl taurates or a combination of these,
   b) 15 to 40% by weight of a pearlescent component, selected from the group consisting of
   fatty acid glycol esters according to the general formula (I)

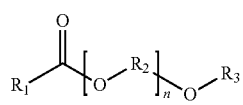

in which $R_1$ is an alkyl radical with 12 to 22 C atoms, $R_2$ is a divalent radical of the formula —$C_2H_4$— or —$C_3H_5$—, $R_3$=H or a radical of the formula

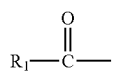

and n is a number from 1 to 10,
fatty acid alkanolamides according to the general formula (II)

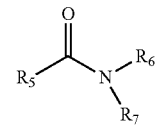

in which $R_5$ is an alkyl radical with 8 to 22 C atoms, $R_6$=H, an alkyl radical with 1 to 4 C atoms, —($CH_2$—$CH_2$—O)$_n$—$R_8$, or —($CH_2$—$CH(CH_3)$—$CH_2$—O)$_n$—$R_8$ with n=1 to 10, $R_7$=H, an alkyl radical with 1 to 4 C atoms, —($CH_2$—$CH_2$—O)$_n$—$R_8$, or —($CH_2$—$CH(CH_3)$—$CH_2$—O)$_n$—$R_8$ with n=1 to 10, and $R_8$=H, methyl, ethyl, n-propyl, i-propyl, n-butyl, i-butyl or t-butyl, and mixtures thereof,
   c) optionally, expedient additives such as preservatives, buffer substances, inorganic or organic electrolytes, alcohols, fatty alcohols, fatty acids and/or their ethoxylates, in particular PEG-x-glyceryl laurates and/or PEG-x-glyceryl cocoates in which x=1 to 10
   and
   d) water in the amount missing to 100% by weight, but not with a concentration higher than 30% by weight.

2. The pumpable aqueous pearlescent concentrate as claimed in claim 1, in which the sum (active content) of the proportions of the dispersant and of the pearlescent component is at least 60% by weight.

3. The pumpable aqueous pearlescent concentrate as claimed in claim 1 in which the sum of the proportions of the water and of the additives is less than 30% by weight based on the total amount of the pearlescent concentrate.

4. The pumpable aqueous pearlescent concentrate as claimed in claim 1, in which the dispersant is from the group consisting of alkyl ether sulfate, alkyl sulfate and/or alkyl sulfonate or a combination of these in a concentration of 35 to 85% by weight.

5. The pumpable aqueous pearlescent concentrate as claimed in claim 1 wherein the pearlescent compound comprises the fatty acid alkanolamides and said alkanolamides comprise at least 60% alkanoic acid derivatives with 12 C atoms.

6. The pumpable aqueous pearlescent concentrate as claimed in claim 1, characterized in that it has a high phase volume ratio.

7. The pumpable aqueous pearlescent concentrate as claimed in claim 1, characterized in that it is completely swollen.

8. The pumpable aqueous pearlescent concentrate as claimed in claim 1, characterized in that it has a high storage stability.

9. The pumpable aqueous pearlescent concentrate as claimed in claim 8, characterized in that its viscosity on a temperature increase to 35° C. increases by not more than 20%.

10. The pumpable aqueous pearlescent concentrate as claimed in claim 1, characterized in that it is free of polyols.

11. A process for the production of a pumpable aqueous pearlescent concentrate, comprising the steps:
    a) introduction of a dispersant selected from the group consisting of alkyl ether sulfates, alkyl sulfates, alkyl sulfonates, mono- and diesters of sulfosuccinic acid, alkyl glycinates, alkyl sarcosinates and/or alkyl taurates or a combination thereof and a pearlescent component comprising one or more pearlescers selected from one or more fatty acid glycol esters according to the general formula (I),

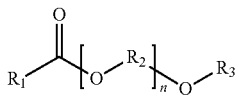
(I)

in which $R_1$ is an alkyl radical with 12 to 22 C atoms
$R_2$ is a divalent radical of the formula —$C_2H_4$— or —$C_3H_5$—,
$R_3$=H or is a radical of the formula

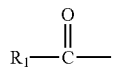

and n is a number from 1 to 10,
and/or of one or more fatty acid alkanolamides according to the general formula (II)

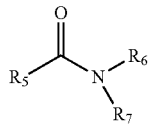
(II)

in which $R_5$ is an alkyl radical with 8 to 22 C atoms,
$R_6$=H, an alkyl radical with 1 to 4 C atoms, —($CH_2$—$CH_2$—O)$_n$—$R_8$, or —($CH_2$—$CH(CH_3)$—$CH_2$—O)$_n$—$R_8$ with n=1 to 10,
$R_7$=H, an alkyl radical with 1 to 4 C atoms, —($CH_2$—$CH_2$—O)$_n$—$R_8$, or —($CH_2$—$CH(CH_3)$—$CH_2$—O)$_n$—$R_8$ with n=1 to 10 and
$R_8$=H, methyl, ethyl, n-propyl, i-propyl, n-butyl, i-butyl or t-butyl,
and optionally water in a first stirring step and thoroughly mixing at 55° C. to 90° C. in a lamellar fluid flow,
b) cooling the mixture by means of a cooling step to below 45° C., in which the pearlescent component crystallizes in the form of a liquid crystalline lamellar structure,
c) intensive mixing of the cooled mixture in a second stirring step and optionally dilution with the remaining amount of water, in which the temperature is kept below 45° C. by reduction of the stirring power and/or cooling of the stirring step,
in which the amount of water employed during the first stirring step and/or during the optional dilution does not exceed 35% by weight based on the concentration of the dispersants and pearlescers employed.

12. The pumpable aqueous pearlescent concentrate as claimed in claim 1, in which the sum (active content) of the proportions of the dispersant and of the pearlescent component is 65 to 85% by weight.

13. The pumpable aqueous pearlescent concentrate as claimed in claim 1, in which the sum (active content) of the proportions of the dispersant and of the pearlescent component is 65 to 85% by weight and the sum of the proportions of the water and of the additives is less than 30% by weight based on the total amount of the pearlescent concentrate.

14. The pumpable aqueous pearlescent concentrate as claimed in claim 1 in which the dispersant is in a concentration of 35 to 85% by weight.

15. The pumpable aqueous pearlescent concentrate as claimed in claim 1 in which the dispersant is in a concentration of 40 to 70% by weight.

16. The pumpable aqueous pearlescent concentrate of claim 5 wherein the concentrate is free of polyols.

17. The pumpable aqueous pearlescent concentrate of claim 13 wherein the concentrate is free of polyols.

* * * * *